US012558465B2

(12) United States Patent
Pleiner et al.

(10) Patent No.: US 12,558,465 B2
(45) Date of Patent: Feb. 24, 2026

(54) TUBE INSERT FOR A HYDRAULIC TUBING SET OF A BLOOD TREATMENT APPARATUS

(71) Applicant: Fresenius Medical Care Deutschland GmbH, Bad Homburg (DE)

(72) Inventors: Franz Pleiner, Estenfeld (DE); Udo Kirstgen, Rottenburg (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 475 days.

(21) Appl. No.: 18/011,379

(22) PCT Filed: Jun. 17, 2021

(86) PCT No.: PCT/EP2021/066357
§ 371 (c)(1),
(2) Date: Dec. 19, 2022

(87) PCT Pub. No.: WO2021/255149
PCT Pub. Date: Dec. 23, 2021

(65) Prior Publication Data
US 2023/0293788 A1     Sep. 21, 2023

(30) Foreign Application Priority Data

Jun. 19, 2020    (DE) .......................... 102020116247.2

(51) Int. Cl.
*A61M 39/00*          (2006.01)
*A61M 1/16*           (2006.01)
(Continued)

(52) U.S. Cl.
CPC .......... *A61M 1/1619* (2014.02); *A61M 39/10* (2013.01); *A61M 39/26* (2013.01); *A61M 2039/0027* (2013.01)

(58) Field of Classification Search
CPC .. A61M 1/1619; A61M 39/10; A61M 39/105; A61M 2039/0027; A61M 2039/0202; A61M 2206/14
See application file for complete search history.

(56) References Cited

U.S. PATENT DOCUMENTS

| | | | |
|---|---|---|---|
| 5,474,544 | A | 12/1995 | Lynn |
| 2005/0261637 | A1 | 11/2005 | Miller |

(Continued)

FOREIGN PATENT DOCUMENTS

| | | |
|---|---|---|
| DE | 8805428 | 7/1988 |
| DE | 102007020859 | 11/2008 |
| DE | 102016117974 | 3/2018 |

OTHER PUBLICATIONS

International Search Report and Written Opinion in International Appln. No. PCT/EP2021/066357, mailed Sep. 24, 2021, 20 pages (with English translation).

*Primary Examiner* — Bradley R Spies
(74) *Attorney, Agent, or Firm* — Fish & Richardson P.C.

(57) ABSTRACT

The present disclosure relates to a tube insert for a dialysis liquid line or a hydraulic tubing set, the tube insert including at least one housing; a first connection point for connecting a tube section of the hydraulic tubing set to the tube insert; a second connection point for connecting a second tube section of the hydraulic tubing set to the tube insert; a third connection point for connecting a fluid receptacle to the tube insert; a main line in fluid communication with the first connection point and with the second connection point; a secondary line in fluid communication with the third connection point; and a deflection element for deflecting the liquid, or parts thereof, flowing in the main line out of the flow direction and towards the secondary line.

20 Claims, 4 Drawing Sheets

(51) Int. Cl.
    *A61M 39/10*      (2006.01)
    *A61M 39/26*      (2006.01)

(56)                 References Cited

U.S. PATENT DOCUMENTS

| | | |
|---|---|---|
| 2014/0207117 A1 | 7/2014 | Ueda et al. |
| 2015/0297880 A1 | 10/2015 | Ogawa et al. |
| 2020/0016314 A1 | 1/2020 | Hacker et al. |

TUBE INSERT FOR A HYDRAULIC TUBING SET OF A BLOOD TREATMENT APPARATUS

CROSS-REFERENCE TO RELATED APPLICATIONS

The present application is the national stage entry of International Patent Application No. PCT/EP2021/066357, filed on Jun. 17, 2021, and claims priority to Application No. DE 10 2020 116 247.2, filed in the Federal Republic of Germany on Jun. 19, 2020, the disclosures of which are expressly incorporated herein in its entirety by reference thereto.

TECHNICAL FIELD

The present disclosure relates to a tube insert according to the preamble of claim 1, a hydraulic tubing set according to the preamble of claim 13 and a blood treatment apparatus according to the preamble of claim 16.

BACKGROUND

During extracorporeal blood treatment, samples of liquids whose composition is of interest are regularly taken, usually from a tube which carries the liquid of interest. Samples are regularly taken from the tube via withdrawal sites especially provided for this purpose, which may also serve as addition sites. They may be designed in a T-shape as so-called T-pieces or have any other suitable shape to be used as tube inserts, (i.e., inserts that are inserted between two tube sections or two tubes to connect them fluidically).

SUMMARY

In addition to a main line through which the liquid to be sampled flows, tube inserts may comprise a secondary line being in fluid communication with the main line, through which a sample of the liquid flowing through the main line may be taken. For this purpose, the secondary line comprises a connection point or junction for connecting its lumen to, e.g., a syringe. In order to again fluid-tightly seal the connection point against the environment after the sample has been taken, for example by using a syringe, and is then sent to the laboratory for evaluation of its sample content, such connection points comprise, in practice, closures or valves. Such valves may for the sake of simplicity be activated (opened) with a Luer lock closure, and designed to be automatically deactivated (closed) when the syringe is removed from the connection point.

An object according to the present disclosure may consist of proposing a further tube insert of this or of a similar type (alternatively: connection piece, tube insert or adapter) to allow taking a sample from a liquid or solution perfusing the tube insert, such as dialysis liquid.

The object may be achieved by a tube insert with the features of claim 1, a hydraulic tubing set with the features of claim 13 and a blood treatment apparatus with the features of claim 16.

The tube insert according to the present disclosure serves to be used in a hydraulic tubing set or a dialysis liquid line or to be part thereof. In this, the tube insert comprises at least one housing with a first connection point for connecting a first tube section of the hydraulic tubing set or of a line section to the tube insert, and a second connection point for connecting a second tube section of the hydraulic tubing set or a line section to the tube insert. The tube insert also comprises a third connection point for connecting a fluid receptacle (syringe, hose, vial, etc.) to the tube insert.

The housing of the tube insert comprises a main line with a longitudinal extension, which serves to conduct a liquid, preferably dialysis liquid, through the tube insert in a flow direction from the first connection point to the second connection point. In this, the liquid flows, during use, preferably along or in the longitudinal extension and/or parallel to a center line of the main line, wherein the main line is in fluid communication with the first connection point and with the second connection point, or respectively with a lumen surrounded by or formed by the first connection point and/or by the second connection point.

The tube insert also comprises at least one secondary line. The secondary line serves to guide at least partial flows or partial quantities of the liquid out of the main line, wherein it is in fluid communication with the third connection point or with a lumen surrounded by the latter. The secondary line is in fluid communication with the main line in a section of the tube insert, referred to herein as the intermediate section, which is arranged between the first connection point and the second connection point. In addition, the secondary line comprises a Luer-activatable valve with a valve housing and a valve body, which are preferably deformable for switching the valve states or for opening or closing the valve as intended.

The first connection point comprises a flowable lumen with a first cross-sectional area; the second connection point comprises a flowable lumen with a second cross-sectional area. The size of the first cross-sectional area may correspond to the size of the second cross-sectional area, be smaller or larger.

The tube insert comprises preferably also at least one deflection element which serves to deflect the liquid flowing in the main line, or parts thereof, when the tube insert is in use. The deflection takes place in the area of the intermediate section and guides the liquid out of the flow direction of the main line, in which the liquid enters the tube insert or its housing through the first connection point, at least temporarily out and in the direction of the secondary line or third connection point.

The hydraulic tubing set according to the present disclosure comprises at least one tube insert according to the present disclosure.

The blood treatment apparatus according to the present disclosure is connected to at least one hydraulic tubing set according to the present disclosure and/or comprises at least one tube insert according to the present disclosure.

Embodiments according to the present disclosure may comprise one, several or all of the following features in any combination, unless this is recognized as being technically impossible by the person skilled in the art. Advantageous developments of the present disclosure are each also subject-matter of the dependent claims.

In all of the following statements, the use of the expression "may be" or "may have" and so on, is to be understood synonymously with "preferably is" or "preferably has," and so on respectively, and is intended to illustrate an embodiment according to the present disclosure.

Whenever numerical words are mentioned herein, the person skilled in the art shall recognize or understand them as indications of numerical lower limits. Unless it leads the person skilled in the art to an evident contradiction, the person skilled in the art shall comprehend for example the specification of "one" as encompassing "at least one". This understanding is also equally encompassed by the present disclosure as the interpretation that a numerical word, for example, "one" may alternatively mean "exactly one", wherever this is evidently technically possible for the person skilled in the art. Both are encompassed by the present disclosure and apply to all numerical words used herein.

Spatial information given here, such as "above", "below", etc., refer in case of doubt to the representation as shown in the herein attached figures.

Whenever an embodiment is mentioned herein, it is then an exemplary embodiment according to the present disclosure, which is not to be understood as limiting.

If it is disclosed herein that the subject-matter of the present disclosure comprises one or several features in a particular embodiment, it is also respectively disclosed herein that the subject-matter according the present disclosure expressly does not comprise this or these features in other embodiments which likewise are according to the present disclosure, e.g., in the sense of a disclaimer. For each embodiment mentioned herein, the opposite embodiment, e.g., formulated as a negation, is also disclosed.

In several embodiments of the tube insert according to the present disclosure, the deflection element is arranged in the main line or can be arranged in the main line such that a liquid flow prevailing in the main line is guided completely or partially out of a projection between the first cross-sectional area of the first connection point with the second cross-sectional area of the second connection point and guided in the direction of the secondary line. A projection may be a cylindrical, also a theoretical, continuation or connection between the first cross-sectional area of the first connection point and the second cross-sectional area of the second connection point.

In some embodiments, the third connection point is designed such that it is possible to connect a fluid receptacle to it or therein, which is or which comprises a syringe with a syringe plunger and syringe cylinder, which in turn may carry a Luer lock connector.

In some embodiments, the third connection point is designed such that it is possible to connect to it or therein a fluid receptacle which comprises a Luer lock connector. Alternatively or in addition, the Luer-activatable valve of the secondary line comprises a Luer lock connector.

In some embodiments, the deflection element in the intermediate section is connected to the inner wall of the main line, arranged on it or manufactured integrally with it, such that a flow of the liquid is not possible between the deflection element and a wall of the intermediate section facing away from the secondary line.

In these embodiments, there is no splitting of the liquid flow (i.e., the entire volume of the liquid flow is diverted in the direction of the secondary line).

In some embodiments, the deflection element extends at least in one section in a direction parallel to the longitudinal extension of the main line and/or along its center line.

In several embodiments, the section extending at least partially in the direction parallel to the longitudinal exten- sion of the main line extends into a central area of the cross-section or into one half of the flow-through lumen of the intermediate section of the tube insert facing the sec- ondary line.

In some embodiments, the deflection element extends at least in one section in a direction vertical the longitudinal extension of the main line.

In several embodiments, the section which extends at least partially in the direction vertical the longitudinal exten- sion of the main line, extends out of the housing of the tube insert according to the present disclosure or out of the projection.

In some embodiments, the deflection element comprises at least one angled section. This preferably comprises an angle between 80° and 100°. An angle from this angular range may serve to generate a turbulent flow or a swirl in the vicinity of the deflection element and thus in the direction of the secondary line towards the Luer-activatable valve.

In several embodiments, the cross-sectional area of the flow-through lumen for the liquid in a cross-section which also comprises the deflection element is at least 80%, preferably at least 90% of the first or of the second cross-sectional area.

In some embodiments, the housing of the tube insert according to the present disclosure comprises a connection which serves to connect, attach and/or center the valve housing of the Luer-activatable valve relative to the housing. The connection may be integral with the housing or arranged thereon.

In several embodiments, the connection comprises or consists of at least two, preferably four, elevations.

In some embodiments, the elevations are arranged spaced from each other in a central area thereof or of the connection, and/or at the front/end face. Thus, for example, gaps or passages may be provided between them and the adjacent elevation(s). The elevations may be, at least in sections, e.g., without material connection with each other. A flushing of a space between them is thus possible, in particular also in one direction, e.g., parallel to the longitudinal extension of the housing and/or parallel to the center line of the main line.

In several embodiments, the elevations are arranged in order not to encircle or surround a space or area between them or delimited by them, in particular not at the front/end face or at their free end, with which they are, e.g., not connected to the housing or with which they continue into the elevation.

In several embodiments of the tube insert according to the present disclosure, the distance between the outer sides of two mutually opposite elevations of the connection essen- tially corresponds to the front/end face inner diameter of the valve housing.

In some embodiments, the valve body, which may be made of or with silicone in this example, of the Luer-activatable valve is in direct contact with the connection.

Intermediate elements are not provided in these embodi- ments, in particular not in the form of a conventional insert for Luer-activatable valves.

In several embodiments, the connection does not have a circumferential end face, in particular no end face that lies in only one plane. In some embodiments, the connection is rather a sequence of elevations on the one hand, and gaps, depressions or recesses, on the other hand alternating in the circumferential direction of the connection.

In some embodiments, the section which extends at least partially in the direction vertical the longitudinal extension of the main line extends into or beyond the connection of the tube insert according to the present disclosure.

In several embodiments, the valve housing of the Luer-activatable valve is connected circumferentially to an outer wall of the housing by its front/end face, preferably welded, preferably ultrasonically welded.

In several embodiments, the valve housing or the second-ary line is limited by the Luer-activatable valve or closed at the front/end face. In some embodiments, the secondary line ends in the Luer-activatable valve (provided the latter is in its closed state). In several embodiments, the secondary line is limited by or due to its connection to the main line or to the intermediate section on the one hand and to the Luer-activatable valve on the other hand. In certain embodiments, the secondary line or the housing section surrounding it or the hose insert with respect to the secondary line, does not comprise a third or further connection, a third or further end, a third or further connection point or opening to the outside or the like.

In some embodiments of the hydraulic tubing set according to the present disclosure, the tube insert is connected to two sections of a dialysis liquid (inlet) line, alternatively to two sections of a dialysate (outlet) line.

In several embodiments of the hydraulic tubing set according to the present disclosure, the latter comprises a dialysis liquid (inlet) line, in others it comprises no other line than the dialysis liquid (inlet) line.

In some embodiments of the hydraulic tubing set according to the present disclosure, the latter comprises a dialysate (outlet) line, in others it comprises no other line than the dialysate (outlet) line.

In several embodiments, the hydraulic tubing set according to the present disclosure is suitable and/or accordingly intended for performing hemodialysis, hemofiltration, hemodiafiltration, plasmapheresis treatment or whole blood adsorption treatment.

In some embodiments, the tube insert according to the present disclosure is inserted between tube sections of the hydraulic tubing set or manufactured integrally therewith. If the tube insert is manufactured integrally with the hydraulic tubing set, all or some of the sections of the tube insert referred to herein as connection points are transition sections between the tube insert and adjacent or continuing tube sections.

In several embodiments, the tube insert according to the present disclosure is permanently connected to tube sections of the hydraulic tubing set, in others it is releasable.

In certain embodiments, the deflection element is not the inner wall of the main line, for example in the area of the first connection point, the second connection point or the intermediate section.

In some embodiments, the radially inner end of the deflection element lies further radially inward than the inner wall of the main line, for example in the area of the first connection point, of the second connection point or of the intermediate section.

In certain exemplary embodiments according to the present disclosure, the deflection element does not have a ring shape.

In certain exemplary embodiments according to the present disclosure, the deflection element is not an aperture-shaped structure.

In certain exemplary embodiments according to the present disclosure, the deflection element does not narrow the flow-through lumen of the intermediate section in a circular manner, for example over the entire inner circumference of the intermediate section.

In certain exemplary embodiments according to the present disclosure, the deflection element is arranged inside the main line such that the liquid perfusing the lumen of the main line may flow in the area of the deflection element in front of it (i.e., in front of the drawing plane of the drawing attached here) as well as behind it (i.e., behind the drawing plane of the drawing attached here).

In certain exemplary embodiments according to the present disclosure, the tube insert is made of plastic, preferably injection molded.

In certain exemplary embodiments according to the present disclosure, the tube insert does not comprise a threedimensional spiral structure for generating turbulence, in particular no recessed cutout in the inner wall of the intermediate section.

In certain exemplary embodiments according to the present disclosure, the deflection element is not designed as a raised bead on the inner wall of the intermediate section, or it is not a thickening of the inner wall.

In several exemplary embodiments according to the present disclosure, the first, the second and/or the third connection point is glued to a tube section, respectively. Alternatively, the connection may be a plug-in or clamping connection or another connection.

When liquids are mentioned herein, this is not to be understood as limiting. The present disclosure also encompasses guiding, deflecting, sampling, etc., of fluids in a broader sense.

The deflection element may have a transition from a first section, which is, e.g., parallel to a center line of the main line, to a second section, which is, e.g., vertical to the first section, which has a radius of 0.05 mm to 0.15 mm, preferably less than 0.11 mm, but preferably at least less than 2 mm, particularly preferably at least less than 1 mm, or may be described thereby. The resulting almost right-angled transition from the first section to the second section is preferably used to generate a turbulent flow at this point, which can result in increased rinsability.

In some embodiments, the secondary line comprises only one lumen, not two or more, which can guide a fluid simultaneously, for instance in parallel streams or partial streams, in the same direction, for instance toward the third connection point or away from the third connection point.

In several embodiments, the main line comprises, in any state of use of the tube insert, a lumen or partial lumen through which a liquid flowing through the main line may flow from the first connection point to the second connection point without having to change its direction and/or without having to flow through sections of the secondary line or of the housing section surrounding it.

In some embodiments, the main line comprises, in each state of use of the tube insert, a lumen or partial lumen through which a liquid flowing through the main line may flow directly from the first connection point to the second connection point.

In some embodiments, the tube insert does not simultaneously have a line leading away from the main line, for instance a deflection line, and a line leading to the main line, for instance an injection line.

Some or all of the embodiments according to the present disclosure may comprise one or more of the advantages mentioned above or below.

Conventional tube inserts (T-pieces), e.g., for the manual sampling of a fluid perfusing the T-piece by a Luer lock connector, always comprise a dead volume in the transition to the connection point of the secondary line in which dead volume fluid may be present that has reached there at an earlier point in time. At this time, the fluid to be sampled may have had different parameter values than at the time of the current sampling. A dead volume may thus mean or lead to the fact that the parameters of the withdrawn sample do not reflect the sample, that measurement results are distorted, or that considerable effort must be made during sampling, since the fluid present in the dead volume must first be manually removed and discarded before usable sample material can be taken from the tube insert or via the tube insert.

By using the present disclosure, the advantages of a Luer-activatable valve, which may be actuated by simply connecting a Luer connector, and the advantages of a suitable T-piece for taking samples from the main line may be combined. This may contribute to an improved rinsability of the line and to an easier sampling.

An advantage of the present disclosure may be that it replaces the function and geometry of an insert body from the prior art as a flow-through counter bearing for the valve body. This may minimize the volume to be rinsed and also contribute to saving material and costs.

The deflection element of the present disclosure directs the flow out of the main line partially or completely (at first) into the secondary line. By suitable selection of the geometries it can be ensured that the flow resistance obtained by the deflection is not higher, or (if desired) higher, than elsewhere in the main line.

By using the present disclosure, a turbulent flow may be generated within the tube insert, by which advantageously all areas of the valve and an optionally available insert to be rinsed may be rinsed.

BRIEF DESCRIPTION OF THE DRAWINGS

The present disclosure is explained below based on the attached drawings, in which identical reference numerals designate identical or similar components. In the partly highly simplified figures, the following applies

DETAILED DESCRIPTION

Figure 1:
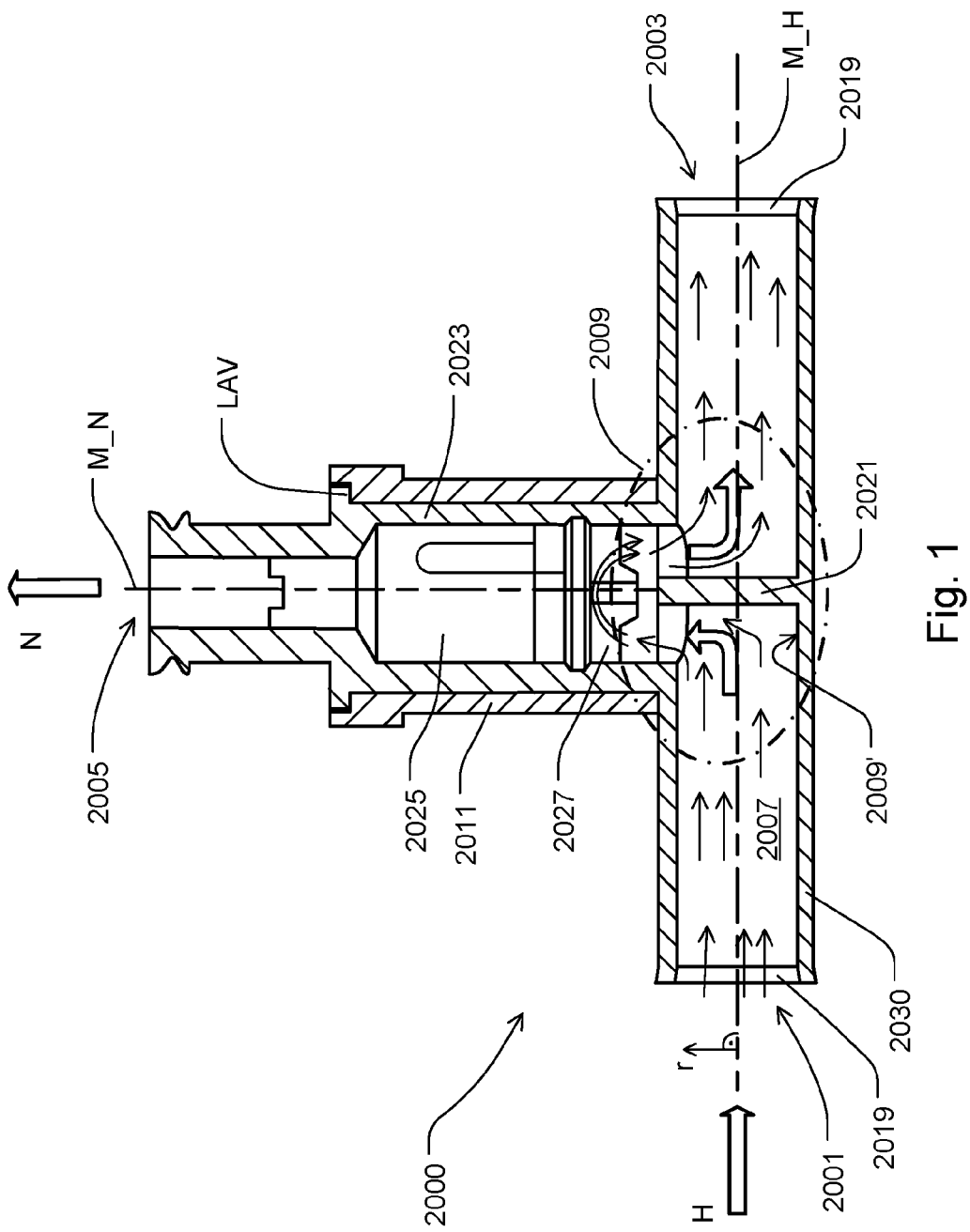
FIG. 1 shows a tube insert according to the present disclosure for a hydraulic tubing set, not shown in FIG. 1, in a first exemplary embodiment in a longitudinal section.
Figure 4:
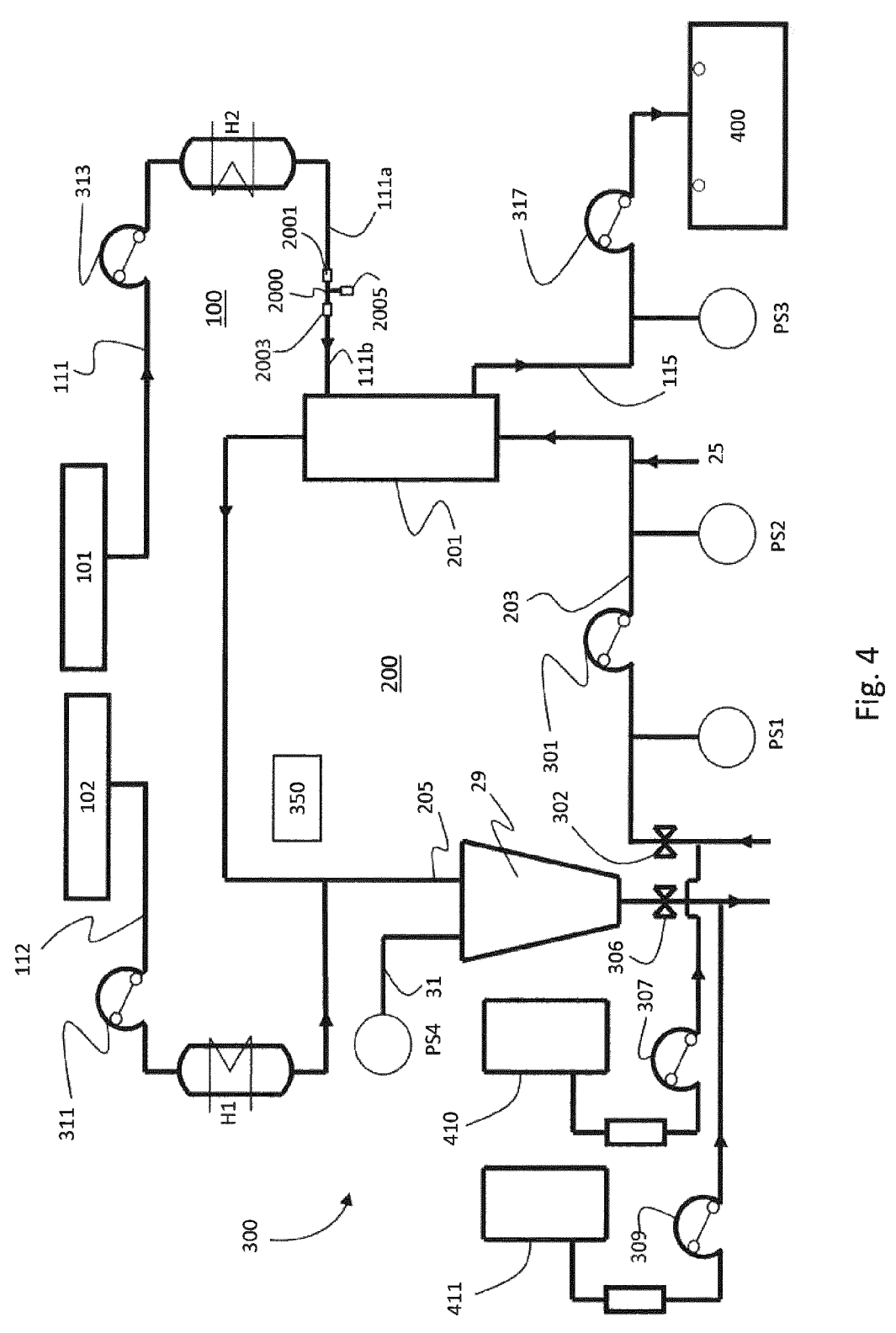
FIG. 4 shows a blood treatment apparatus according to the present disclosure with a hydraulic tubing set according to the present disclosure.

FIG. 1 shows the tube insert 2000 according to the present disclosure with a housing 2030 for a hydraulic tube, not shown in FIG. 1, or a hydraulic tubing set, e.g., the hydraulic tubing set 100 shown in FIG. 4, in a first exemplary embodiment in a longitudinal section.

The tube insert 2000 comprises a first connection point 2001, by which a first tube section 111a (see FIG. 4), e.g., a line 111 for dialysis liquid of the hydraulic tubing set 100, may be connected to the tube insert 2000.

The tube insert 2000 comprises a second connection point 2003 with which a second tube section 111b (see FIG. 4) of the hydraulic tubing set 100 may be connected to the tube insert 2000.

The tube insert 2000 has a third connection point 2005, by which a syringe, a line (not shown) or another fluid receptacle for taking a sample from the hydraulic tubing set 100 may be connected to the tube insert 2000.

The tube insert 2000 comprises a main line 2007 for guiding a liquid, preferably dialysis liquid, through the tube insert 2000. The main line 2007 is in fluid communication with the first connection point 2001 and with the second connection point 2003. The liquid may flow, e.g., in the direction of arrow H into the main line 2007.

The tube insert 2000 comprises a longitudinal extension which runs parallel to the center line M_H of the main line 2007. Das Schlaucheinsatzstück 2000 weist eine Quererstreckung oder radiale Erstreckung auf, welche in der mit r bezeichneten Richtung verläuft und senkrecht zur Längserstreckung steht. The tube insert 2000 comprises a transverse or radial extension, which runs in the direction marked r and is vertical the longitudinal extension.

The tube insert 2000 comprises a secondary line 2011. It serves as a receptacle for a Luer-activatable valve LAV (alternatively: Luer-activated valve LAV), which comprises a valve housing 2023 and a valve body 2025 or consists of these as the only separable elements, may have such a valve or may be formed by such a valve.

The tube insert 2000 comprises an intermediate section 2009, which in FIG. 1 is circumscribed by a broken line and through which the main line 2007 passes, or which is part of the main line 2007. Main line 2007 and secondary line 2011 meet in the intermediate section 2009, which is located between the two, or in which both are in fluid communication with each other when the Luer-activatable valve LAV is open.

The secondary line 2011 serves to enable taking a sample of the liquid, which perfuses the main line 2007, out of the main line 2007 in the direction of the arrow N along the secondary line 2011, e.g., parallel to its center line M_N.

A Luer-activatable valve (LAV) (also referred to as a Luer-activated valve) may be a plug-in valve being closed in a basic state and designed to be activated, (i.e., opened), when it is connected or when its valve housing is connected to a Luer lock connector, which may be, for example, a Luer lock connector of a fluid receptacle or fluid container. Such a Luer-activatable valve LAV thus opens, e.g., when connecting the secondary line 2011, e.g., with a fluid receptacle or a fluid container, which carries a Luer lock connector and closes again only when its Luer lock connector is disconnected from the third connection point. The Luer lock connector of the Luer-activatable valve LAV can be a female connector as shown in the figures, the Luer lock connector of the fluid receptacle or fluid container may be a male connector, or vice versa.

The secondary line 2011 is also in fluid communication with the third connection point 2005.

The first connection point 2001 comprises a flow-through lumen with a first cross-sectional area and an inner wall. The inner wall encloses an interior of the first connection point 2001. In the example of the first connection point 2001, the interior corresponds to its flow-through lumen.

The second connection point 2003 comprises a flow-through lumen with a second cross-sectional area and an inner wall. The inner wall encloses an interior of the second connection point 2003. In the example of the second connection point 2003, the interior corresponds to its flow-through lumens.

The intermediate section 2009 comprises a flow-through lumen with a third cross-sectional area and an inner wall 2009'. The inner wall 2009' encloses an interior of the intermediate section 2009. In the example of the intermediate section 2009 in FIG. 1, the interior does not correspond to its flow-through lumen. The cross-sectional area of the interior is rather larger by the cross-sectional area of a deflection element 2021 than the flow-through cross-sectional area of the lumen, as far as the deflection element 2021 extends into the interior. If the deflection element 2021 of FIG. 1 is ignored, then the interior in FIG. 1 would correspond to the flow-through lumen.

The center line M_H of the main line 2007 which is optionally straight here (roughly defined by the center points of the first and second cross-sectional areas, see above) corresponds to the longitudinal axis of the main line 2007 and its axial direction and runs in the direction of the longitudinal extension of the tube insert 2000.

As FIG. 1 further shows, the deflection element 2021 projects into the interior of the intermediate section 2009. In this, the deflection element 2021 in this embodiment is not to be understood as a thickening or narrowing of the wall of the tube insert 2000, but rather as a narrowing of the lumen of the main line 2007 in the area of the intermediate section 2009 with the aim of deflecting the flow path of a liquid perfusing the main line 2007 in the direction towards the secondary line 2011. This serves the purpose of shifting the flow path of a liquid perfusing the main line 2007 as close as possible to the Luer-activatable valve LAV arranged in the secondary line 2011, e.g., close to an insert body 2027 thereof and/or through it. This fluid flow is indicated by wide arrows.

This shifting may be achieved in that, as exemplarily shown in FIG. 1, the deflection element 2021 limits, narrows or occludes part of the diameter or of the cross-sectional area of the main line 2007.

The flow of liquid deflected in this way flows, as indicated in FIG. 1, to overcome the deflection element 2021 wholly or partly out of the main line 2007, which may be understood as a straight or cylindrical connection between the first cross-sectional area and the second cross-sectional area, into the secondary line 2011 and beyond the deflection element 2021 back into the main line 2007.

The first connection point 2001 and/or the second connection point 2003 may optionally each have a step, bevel or chamfer 2019 of their inner wall and/or outer wall, which may facilitate the connection of the respective connection point with a tube section.

As can be seen in FIG. 1, the deflection element 2021 herein is not for example a section that is continuously adjacent to the inner wall 2009' of the intermediate section 2009. Whereas the inner wall 2009' delimits the interior of the intermediate section 2009, the deflection element 2021 rather protrudes beyond the inner wall 2009' and into the interior of the intermediate section 2009.

Optionally, the deflection element 2021 is not a structure that is ring-shaped in a cross section of the intermediate section 2009.

Optionally, the deflection element 2021 is not an aperture-shaped structure with a central passage opening, which forms a passage for the liquid in a cross section of the intermediate section 2009, but which would contact the inner wall 2009' in a circle along its outer circumference, for example, along the entire inner circumference of the intermediate section 2009.

Optionally, the deflection element 2021 is arranged in the interior of the main line 2007 such that the liquid which perfuses the lumen of the main line 2007 cannot flow laterally past the deflection element 2021 in the area thereof (i.e., in front of the drawing plane or behind the drawing plane).

An optional feature of the tube insert 2000 according to the present disclosure is that the flow-through area of the tube insert 2000 in the region of the intermediate section 2009 is not less than the flow-through area of the main line 2007 in the region of the first connection point 2001 and/or in the region of the second connecting point 2003, although the flow-through area of the main line 2007 in this section is less than upstream or downstream thereof. According to the present disclosure, various designs are envisaged for this purpose. An option is shown in FIG. 1.

The option shown in FIG. 1 shows the deflection element 2021, which, similar to a small plate or disc coming from the inner wall 2009', restricts the flow cross-section of the lumen of the main line 2007 which is why the flow in the intermediate section 2009 optionally shifts completely into the secondary line 2011, where it runs near the Luer-activatable valve LAV and upstream of it and/or in it causes a flushing of the area of the Luer-activatable valve LAV.

The design of the deflection element 2021 as shown in FIG. 1 has, in addition to the function of shifting the flow, also the effect of swirling the flow upstream and/or downstream of the deflection element 2021, which may contribute to further improved mixing and rinsing.

Figure 2:
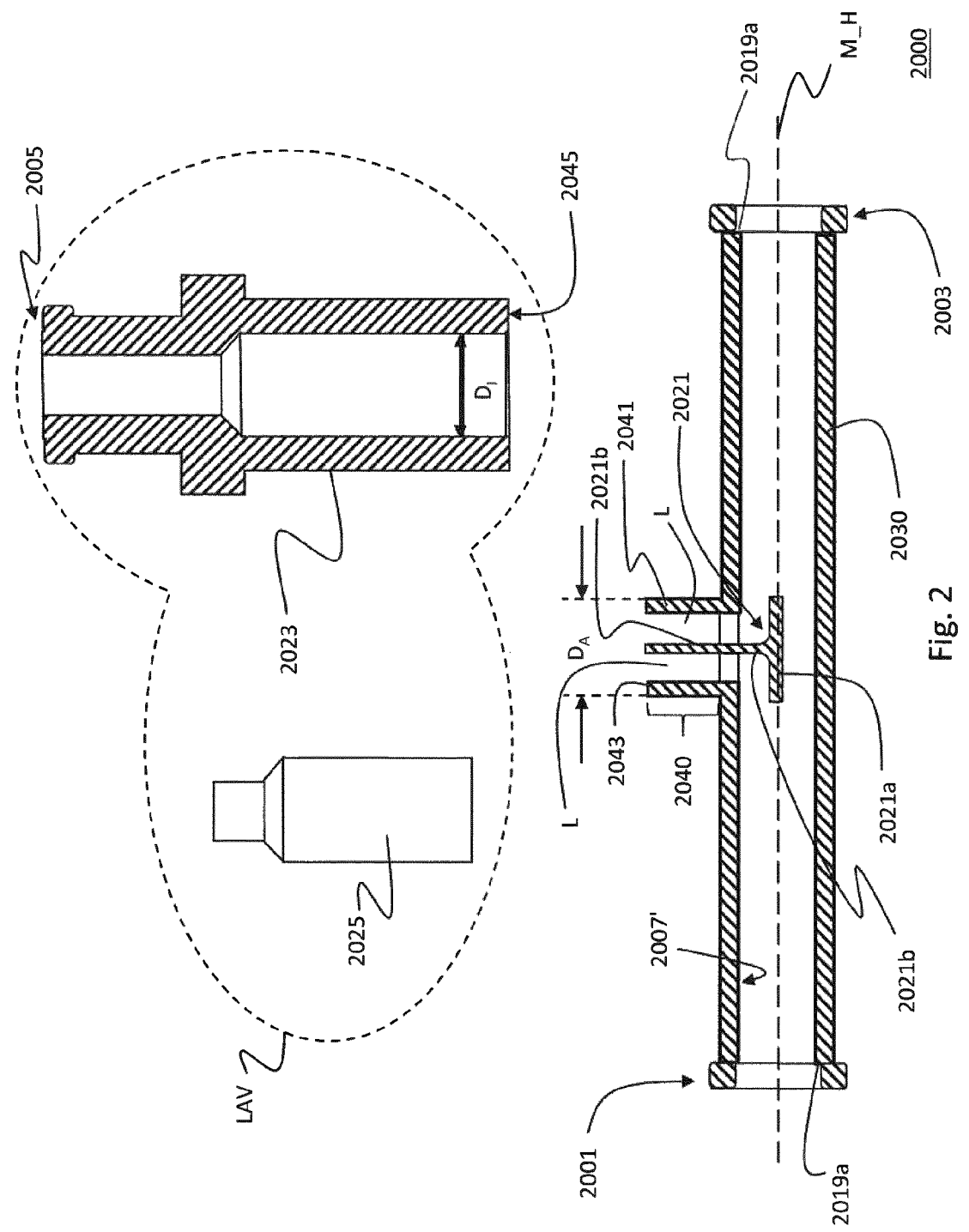
FIG. 2 shows the elements of a tube insert according to the disclosure in a second exemplary embodiment in a longitudinal section.

The deflection element 2021, which is shown in FIG. 1 in disc form, may alternatively be of a different shape and/or arrangement, preferably while retaining all other features of the embodiment shown in FIG. 1, such as shown in FIG. 2.

FIG. 2 shows a tube insert 2000 according to the present disclosure in a second embodiment. The elements of the tube insert 2000 according to the present disclosure in FIG. 2 are shown separately for the sake of clarity.

The deflection element 2021 in FIG. 2, unlike that in FIG. 1, comprises not only a section 2021*b* oriented vertical (or approximately vertical) to the center line M_H but also a section 2021*a* oriented parallel (or approximately parallel) to the center line M_H. The angle between the vertical section 2021*b* and the parallel section 2021*a* may thus optionally be 90°. However, angles deviating therefrom, and in particular angles between 80° and 100°, are also encompassed by the present disclosure.

The deflection element 2021, which here optionally comprises the shape of an anchor or an L-piece, or a T-piece, may be produced integrally with a section of the housing 2030, for example with its wall, and/or may be connected therewith in a force-fit and/or form-fit manner.

At the transition from its parallel section 2021*a* to its vertical section 2021*b*, the T-shaped deflection element 2021 may have an inner radius of approximately 0.1 mm, but preferably less than 2 mm, particularly preferably less than 1 mm. The resulting almost right-angled transition from parallel section 2021*a* to vertical section 2021*b* serves to generate a turbulent flow at this point, which may result in increased rinsability.

The vertical section 2021*b* of the deflection element 2021, or another section of the deflection element 2021, may project beyond an outer wall of the cylindrically designed part of the housing 2030, e.g., beyond its wall bounding or delimiting the main line 2007 or the intermediate section 2009, as shown in FIG. 2. The function of the section projecting in this way is further explained below.

The housing 2030 of the tube insert 2000 comprises a connection 2040, which serves to connect the Luer-activatable valve LAV, its valve housing 2023 or another component of the secondary line 2011 or of the third connection point 2005.

This connecting to connection 2040 may be made by simply pushing the valve housing 2023 onto the connection 2040. For this purpose, an inner diameter $D_I$ of the valve housing 2023 may be designed to fit exactly on an outer diameter $D_A$ of connection 2040, for example with an inner diameter $D_I$ slightly smaller than the outer diameter $D_A$.

The outer diameter $D_A$ of the connection 2040 may be measured between the outer limitation or extension of a first elevation 2041 of the connection 2040, which rises beyond the outer wall of the wall of the housing 2030 bounding the main line 2007, and the outer limitation of a second elevation 2043 of the connection 2040 to which the same applies.

A front/end face or surface 2045 of the valve housing 2023 may preferably be curved or extend in three dimensions, which is not shown in FIG. 2. Such a shape may allow the front/end face or surface 2045 to fit as completely as possible to an outside of the curved housing 2030.

This connection between the front/end face or surface 2045 of the valve housing 2023 and the housing 2030 of the main line 2007 may be fluid-tight. It may be or may have been made, for example, by plastic welding, ultrasonic welding or other suitable methods.

The deflection element 2021 may be connected in particular in its vertical section 2021b to the wall or to another section of the housing 2030 or may be manufactured in one piece, for example by integral production, e.g., during an injection molding process.

As further shown in FIG. 2, the two elevations 2041, 2043, and optionally other elevations, if any, do not touch each other in their free sections, e.g. their free ends pointing upwards in FIG. 2, whereas they may be connected to, or may emerge from, the outer wall of the housing 2030 with their opposite ends pointing downwards in FIG. 2.

The gaps L thus created between the free ends and/or between intermediate sections of the elevations 2041, 2043 located between the two ends allow fluid to flow between the elevations 2041, 2043 in a direction vertical their longitudinal extension (i.e., in a direction out of or into the drawing plane with respect to FIG. 2 and through the gaps L).

Figure 3:
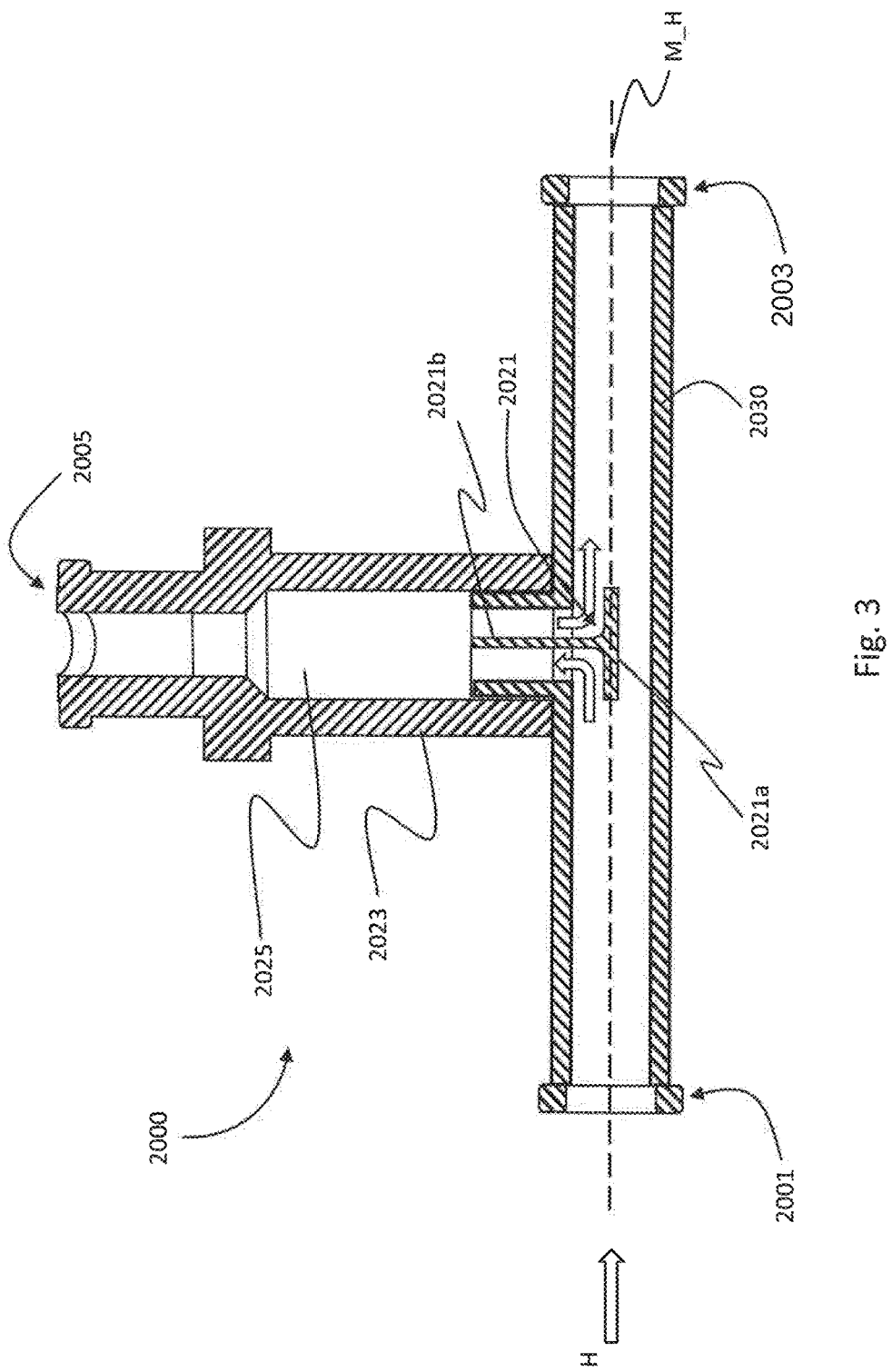
FIG. 3 shows the tube insert according to the present disclosure from FIG. 2 in a state of use in a longitudinal section.

The elevations 2041, 2043 are preferably designed to serve as a counter bearing or receptacle for the end section of the valve body 2025, or sections thereof, pointing downwards in FIG. 2. If the valve body 2025 is inserted into the valve housing 2023 of the Luer-activatable valve LAV and positioned as shown in FIG. 3, the connection 2040 being flow-through in the described manner due to the gaps L, allows rinsing and/or washing around of the valve body 2025. An insert body 2027, which is provided in Luer-activatable valves of the prior art and, as shown in FIG. 1, may also be provided in embodiments according to the present disclosure in order to serve as a counter bearing for the valve body 2025, is not required for this solution according to the present disclosure. Nevertheless, it may be provided.

As shown in FIG. 2, the inner wall 2007' of the main line 2007 comprises an optional stop 2019a, against which a tube, not shown in FIG. 2, which is to be inserted into the first connection point 2001 or into the second connection point 2003, may be pushed.

The herein exemplary ring-shaped stop 2019a may, in use, be in contact with the front/end face of the tube, not shown, which is also ring-shaped. The height of the stop 2019a may advantageously be selected such that the inner wall of the tube continues steplessly or seamlessly in the inner wall 2007' of the section of the inner wall 2007' adjoining the stop 2019a to the right or to the left, respectively.

Such a stop may also be provided in any other embodiment according to the present disclosure.

Such a stop 2019a may be provided in any embodiment according to the present disclosure, optionally in combination with a bevel or chamfer 2019.

FIG. 3 shows the tube insert 2000 according to the present disclosure in the second embodiment of FIG. 2. In this, the elements of the tube insert 2000 according to the present disclosure are shown being ready-for-use assembled.

As already explained in relation to FIG. 2, the valve body 2025 rests directly, or optionally indirectly, on sections of the connection 2040, here, e.g., the elevations 2041, 2043 and possibly others serve as counter bearings for the insert body 2025 when it is pressurized in an up-down direction in FIG. 3 for its switching between the valve states (open/closed). They may also ensure a predetermined minimum distance between the valve body 2025 and, for example, the housing 2030.

As already mentioned in relation to FIG. 2, sections of connection 2040, here, e.g., the elevations 2041, 2043 and possibly others may ensure or favor centering, holding and/or fixing the valve housing 2023.

Finally, reference is made to the function of the free end of section 2021b, which, as here in FIG. 3, is optionally vertical the center line of the main line 2007 or may take a different angle to it. It is also arranged to serve as a counter bearing for the valve body 2025 when force is applied to it in an up-down direction (relative to FIG. 3).

FIG. 4 shows a highly simplified representation of a flow chart of a blood treatment apparatus 300 according to the present disclosure, optionally connected to an extracorporeal blood tubing set 200.

The extracorporeal blood tubing set 200 comprises a first line or blood withdrawal line 203, here in the form of an arterial line section.

The first line 203 is in fluid connection with a blood treatment device, here a blood filter 201, which comprises a dialysis liquid chamber and a blood chamber, which are separated from each other by a mostly semi-permeable membrane. Corresponding retainers or holders, e.g., for the blood filter, which is usually in the form of a cartridge, may be provided on the outer wall of the blood treatment apparatus 300, for example in the form of clamps, slots, etc.

The extracorporeal blood tubing set 200 also comprises at least one second line or blood return line 205, here in the form of a venous line section. Both the first line 203 and the second line 205 serve as their connection to the vascular system of the patient (not shown).

The first line 203 is optionally connected to a (first) tube clamp 302 for blocking or closing the line 203. The second line 205 is optionally connected to a (second) tube clamp 306 for blocking or closing the line 205.

The blood treatment apparatus 300 which is represented in FIG. 4 only by some of its devices and merely schematically, comprises a blood pump 301. During the patient's treatment, the blood pump 301 conveys blood through sections of the extracorporeal blood tubing set 200 and towards the blood filter 201. This is illustrated by the small arrows, which generally indicate the flow direction in each of the figures.

Using a pump 313 for dialysis liquid, which may be designed as a roller pump, as an otherwise occluding pump, a solution, which may be dialysis liquid, is guided from a first source 101, for example a bag, along the dialysis liquid inlet line 111 towards the blood filter 201. In this, the dialysis liquid may optionally be guided through a heating element such as a tube heater or the optionally provided bag heater H2, which is preferably part of the blood treatment apparatus 300 and comprises for example a heating bag.

The first source 101 may be, e.g., a bag or a container. The first source 101 may also be a fluid line from which ready, generated or mixed fluid is provided on-line and/or continuously, for example, a hydraulic outlet or hydraulic connection port of the blood treatment apparatus 300, a hospital water connection or the like.

A further source 102 with substituate liquid may optionally be provided. It may correspond to the first source 101 or be a separate source. The pump 311 is provided to deliver liquid out of the further source 102, for example a bag, and optionally via a heating element such as a tube heater or the optionally provided bag heater H1, which is preferably part of the blood treatment apparatus 300, and comprises, e.g., a heating bag, by a substitute liquid line 112 in predilution upstream of the blood filter 201 or (as shown here) in postdilution downstream of the blood filter 201 into the blood tubing set 200.

A control device or closed-loop control device 350 of the blood treatment apparatus 300 being only roughly outlined may be configured to control or regulate the blood treatment session.

In addition to the above-mentioned blood pump 301 and the pump 313 for dialysis liquid, the arrangement shown in FIG. 4 further comprises purely optionally a series of further pumps, respectively optional, namely pump 317 for discharging dialysate. It conveys dialysate, for example along a line 115 for the dialysate into a basin or a collection bag 400.

The dialysis fluid liquid line 111 may be connected with a section 111*a* thereof to the first connection point 2001 of the tube insert 2000. The second connection point 2003 of the tube insert 2000 may be connected to a second section 111*b* of the dialysis liquid line 111.

Upstream of the blood pump 301, an optional arterial sensor PS1 is provided. During a patient's treatment it measures the pressure in the arterial line.

Downstream of the blood pump 301, but upstream of the blood filter 201 and, if provided, upstream of an addition site 25 for Heparin, a further pressure sensor PS2 is optionally provided. It measures the pressure upstream of the blood filter 201 ("pre-blood filter").

Again, a further, optional pressure sensor to measure the pressure downstream of the blood filter 201 may be provided as PS3 downstream of the blood filter 201, however preferably upstream of the pump 317.

Blood, which leaves the blood filter 201, passes through an optional venous blood chamber 29, which may comprise a de-aeration device 31 and/or a further pressure sensor PS4.

The control device or closed-loop control device 350 shown in FIG. 4 may be in wired or wireless signal communication with any of the components mentioned herein—especially or in particular with the blood pump 301—for controlling or regulating the blood treatment apparatus 300.

Optionally, pumps 307 and 309 are provided which supply a calcium solution ("Ca") from a calcium solution bag 411 or citrate solution ("Ci") from a citrate solution bag 410 to the blood return line 205 or to the blood withdrawal line 203, respectively.

LIST OF REFERENCE NUMERALS

2000 tube insert
2001 first connection point
2003 second connection point
2005 third connection point
2007 main line
2007' inner wall
2009 intermediate section
2009' inner wall
2011 secondary line
2019 bevel or chamfer
2019*a* stop
2021 deflection element
2021*a* parallel section
2021*b* vertical section
2023 valve housing
2025 valve body
2027 insert body
2030 housing

2040 connection
2041 elevation
2043 elevation
2045 front/end face or surface
25 addition point (Heparin)
29 venous blood chamber
31 de-aeration device
100 hydraulic tubing set
101 first source
102 further source
111 line for dialysis liquid
111*a* first line or tube section
111*b* second line or tube section
112 substitute liquid line
115 line for dialysate, filtrate
200 blood tubing set
201 hemofilter or blood filter or dialyzer
203 blood withdrawal line
205 blood return line
300 blood treatment apparatus
301 blood pump
302 first tube clamp
306 second tube clamp
307 pump for citrate solution
309 pump for calcium solution
311 pump
313 pump for dialysis liquid
317 pump for dialysate, filtrate
350 control device
400 collecting bag, basin
410 source for citrate solution
411 source for calcium solution
$D_A$ space, outer diameter of the connection
$D_I$ inner diameter at a front/end face, inner diameter of the valve housing
H1 heating element; bag heater
H2 heating element; bag heater
H inflow direction of the liquid into the main line
N outflow direction of the liquid from the secondary line
L gap
LAV Luer-activated valve; Luer-activatable valve
M_H center line of the main line
M_N center line of the secondary line
PS1 to PS4 pressure sensors
r radial direction or transverse extension of the main line

The invention claimed is:

1. A tube insert for a dialysis liquid line or a hydraulic tubing set, the tube insert comprising:

a housing;

a first connection point configured to connect a first tube section of the dialysis liquid line or of the hydraulic tubing set to the tube insert, the first connection point comprising a first flow-through lumen with a first cross-sectional area;

a second connection point configured to connect a second tube section of the dialysis liquid line or of the hydraulic tubing set to the tube insert, the second connection point comprising a second flow-through lumen with a second cross-sectional area;

a third connection point configured to connect a fluid receptacle to the tube insert;

a main line configured to guide a liquid through the tube insert in a flow direction from the first connection point to the second connection point, the main line comprising a longitudinal extension in fluid communication with the first connection point and with the second connection point;

a secondary line configured to guide at least a portion of the liquid out of the main line, wherein the secondary line is in fluid communication with the third connection point and is in fluid communication with the main line in an intermediate section of the tube insert arranged between the first connection point and the second connection point, the secondary line comprising a Luer-activatable valve (LAV), the LAV comprising:

a valve housing; and a valve body; and a deflection element configured to deflect at least a portion of the liquid flowing in the main line out of the flow direction and towards the secondary line, wherein a portion of the main line comprising the deflection element comprises a third cross-sectional area that is at least 80% of the first cross-sectional area.

2. The tube insert of claim 1, wherein the liquid is dialysis liquid.

3. The tube insert of claim 1, wherein the liquid flows in the longitudinal extension.

4. The tube insert of claim 1, wherein the liquid flows parallel to a center line of the main line.

5. The tube insert of claim 1, wherein the deflection element is arranged or arrangeable in the main line to guide the liquid flowing in the main line to flow completely or partially out of a projection between the first flow-through lumen of the first connection point and the second flow-through lumen of the second connection point and in a direction of the secondary line.

6. The tube insert of claim 1, wherein the housing comprises a connection for connecting the valve housing of the LAV to the housing, wherein the connection is configured to fit the valve housing on the housing or center the valve housing on the housing.

7. The tube insert according to claim 6, wherein the connection comprises at least two elevations, wherein the at least two elevations are arranged in a central region of the connection, on a front/end face of the connection, or both in the central region of the connection and on the front/end face of the connection, wherein adjacent elevations of the at least two elevations are spaced apart from one another.

8. The tube insert of claim 7, wherein the at least two elevations comprise four elevations.

9. The tube insert of claim 6, wherein the valve body of the LAV is in direct contact with the connection.

10. The tube insert of claim 6, wherein the connection is open-ended.

11. The tube insert of claim 6, wherein a section extending at least partially in a direction vertical to the longitudinal extension of the main line extends into or beyond the connection.

12. The tube insert of claim 1, wherein the fluid receptacle comprises a Luer lock connector or wherein the LAV of the secondary line comprises the Luer lock connector.

13. The tube insert of claim 1, wherein at least one section of the deflection element extends in a direction parallel to the longitudinal extension of the main line or in a direction vertical the longitudinal extension of the main line.

14. The tube insert of claim 13, wherein the at least one section of the deflection element extends at least partially in the direction vertical the longitudinal extension of the main line and extends out of the housing.

15. The tube insert of claim 1, wherein the deflection element comprises at least one section that is bent or angled.

16. The tube insert of claim 15, wherein the at least one section of the deflection element is bent or angled at an angle between 80° and 100°.

17. A hydraulic tubing set comprising at least one tube insert, the at least one tube insert comprising:

a housing;

a first connection point configured to connect a first tube section of the hydraulic tubing set to the tube insert, the first connection point comprising a first flow-through lumen with a first cross-sectional area;

a second connection point configured to connect a second tube section of the hydraulic tubing set to the tube insert, the second connection point comprising a second flow-through lumen with a second cross-sectional area;

a third connection point configured to connect a fluid receptacle to the tube insert;

a main line configured to guide a liquid through the tube insert in a flow direction from the first connection point to the second connection point, the main line comprising a longitudinal extension in fluid communication with the first connection point and with the second connection point;

a secondary line configured to guide at least a portion of the liquid out of the main line, wherein the secondary line is in fluid communication with the third connection point and is in fluid communication with the main line in an intermediate section of the tube insert arranged between the first connection point and the second connection point, the secondary line comprising a Luer-activatable valve (LAV), the LAV comprising:

a valve housing; and a valve body; and a deflection element configured to deflect at least a portion of the liquid flowing in the main line out of the flow direction and towards the secondary line, wherein a portion of the main line comprising the deflection element comprises a third cross-sectional area that is at least 80% of the first cross-sectional area.

18. The hydraulic tubing set of claim 17, wherein the tube insert is connected to two sections of a dialysis liquid line or to two sections of a dialysate line.

19. The hydraulic tubing set of claim 17, wherein the hydraulic tubing set is configured for hemodialysis, hemofiltration, hemodiafiltration, plasmapheresis treatment, or whole blood adsorption treatment.

20. A blood treatment apparatus comprising at least one tube insert comprising:

a housing;

a first connection point configured to connect a first tube section of a dialysis liquid line or of the hydraulic tubing set to the tube insert, the first connection point comprising a first flow-through lumen with a first cross-sectional area;

a second connection point configured to connect a second tube section of the dialysis liquid line or of the hydraulic tubing set to the tube insert, the second connection point comprising a second flow-through lumen with a second cross-sectional area;

a third connection point configured to connect a fluid receptacle to the tube insert;

a main line configured to guide a liquid through the tube insert in a flow direction from the first connection point to the second connection point, the main line comprising a longitudinal extension in fluid communication with the first connection point and with the second connection point;

a secondary line configured to guide at least a portion of the liquid out of the main line, wherein the secondary line is in fluid communication with the third connection point and is in fluid communication with the main line in an intermediate section of the tube insert arranged between the first connection point and the second connection point, the secondary line comprising a Luer-activatable valve (LAV), the LAV comprising:

a valve housing; and a valve body; and a deflection element configured to deflect at least a portion of the liquid flowing in the main line out of the flow direction and towards the secondary line, wherein a portion of the main line comprising the deflection element comprises a third cross-sectional area that is at least 80% of the first cross-sectional area.

\* \* \* \* \*